United States Patent [19]

Sellin et al.

[11] Patent Number: 4,963,677

[45] Date of Patent: Oct. 16, 1990

[54] HETEROCYCLIC LACTAM COMPOUNDS

[75] Inventors: Lawrence Sellin; Reijo J. Backstrom, both of Helsinki; Kalevi E. Heinola, Jarvenpaa; Erkki J. Honkanen, Vantaa; Tord K. W. Langenskiold, Espoo; Irma O. Ojala, Helsinki; Aino K. Pippuri; Jarmo J. Pystynen, both of Espoo, all of Finland

[73] Assignee: Orion Corporation Ltd., Espoo, Finland

[21] Appl. No.: 268,450

[22] Filed: Nov. 8, 1988

Related U.S. Application Data

[63] Continuation-in-part of Ser. No. 222,754, Jul. 22, 1988, abandoned, which is a continuation of Ser. No. 139,539, Dec. 30, 1987, abandoned.

[51] Int. Cl.$^5$ .................. C07D 239/70; C07D 471/04
[52] U.S. Cl. ........................................ 544/247; 546/83
[58] Field of Search ........................... 544/247; 546/83

[56] References Cited

U.S. PATENT DOCUMENTS

| | | | |
|---|---|---|---|
| 3,714,170 | 1/1973 | Dohmori et al. | 546/83 |
| 3,954,775 | 5/1976 | Agui et al. | 546/83 X |
| 4,522,947 | 6/1985 | Musser et al. | 546/83 X |
| 4,666,923 | 5/1987 | Hölck et al. | 514/338 |
| 4,695,567 | 9/1987 | Mertens et al. | 514/253 |
| 4,698,346 | 10/1987 | Musser et al. | 546/83 X |
| 4,710,510 | 12/1987 | Mertens et al. | 514/354 |
| 4,730,003 | 3/1988 | von der Saal et al. | 514/387 |

FOREIGN PATENT DOCUMENTS

| | | |
|---|---|---|
| 0189103 | 7/1966 | European Pat. Off. |
| 0161632 | 11/1985 | European Pat. Off. |
| 0186010 | 7/1986 | European Pat. Off. |
| 0214592 | 3/1987 | European Pat. Off. |
| 0263352 | 4/1988 | European Pat. Off. |
| 3410168 | 9/1985 | Fed. Rep. of Germany |
| 218622 | 2/1985 | German Democratic Rep. ................. 544/247 |
| 51-8296 | 1/1976 | Japan ................. 546/83 |
| 1267588 | 1/1985 | Japan . |

OTHER PUBLICATIONS

Chemical Abstracts, vol. 106, No. 13, 30th Mar. 1987, p. 649, column 1, D. R. Shridhar et al., "Synthesis and Anthelmintic Activity of Substituted Imidazo(4,5-g-)-1,4-Benzoxazin-3-Ones...".

*Primary Examiner*—John M. Ford
*Assistant Examiner*—Catherine Scalzo
*Attorney, Agent, or Firm*—Wegner & Bretschneider

[57] ABSTRACT

A compound of the formula

I or

II and pharmaceutically acceptable salts thereof, in which A is $-N=N-NH-$, $-X-C(R_2)=N-$, $-N=C(R_2)-X-$, $-X-C(R_2)-CH(R_2)=N-$ or $-N=C(R_2)-CH(R_2)-X-$, wherein X is sulphur, oxygen or nitrogen and $R_2$ is provided that where two $R_2$-groups are present in the A group one of the $R_2$ groups is hydrogen, amino, substituted amino, $C_{1-6}$alkyl, substituted acylamino or one of the following groups:

(Abstract continued on next page.)

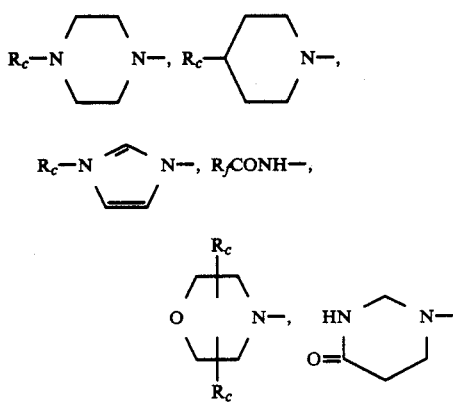

wherein $R_a$ is hydrogen, amino, substituted amino, $C_{1-6}$alkoxy, heterocyclic five membered ring or —NHCOR', wherein R' is $C_{1-6}$alkyl, aryl or heterocyclic five membered ring, $R_b$ is hydrogen, $C_{1-6}$alkoxy, $C_{1-6}$alkylthio or hydroxy, $R_c$ is hydrogen, $C_{1-6}$alkyl or oxygen and $R_d$ is $C_{1-6}$alkyl or oxygen, $R_e$ is hydrogen, hydroxy or $C_{1-6}$alkoxy, $R_f$ is $C_{1-6}$alkyl, provided that where two $R_2$ groups are present in the A group, one of the $R_2$ groups is hydrogen; B is —$(CH_2)_m$—$C(R_3R_4)$—$(CH_2)_n$—, —$C(R_3)$=CH—, —CH=$C(R_3)$—, —O—$[C(R_3R_4)]_n$—, —$[C(R_3R_4)]_n$—O—, —S—$[C(R_3R_4)]_n$— or —$[C(R_3R_4)]_n$—S— wherein $R_3$ and $R_4$, which can be independently the same or different, are hydrogen, $C_{1-6}$alkyl, aryl (preferably phenyl) or pyridyl and m and n are independently zero or 1; D is either oxygen or sulphur; the two R-groups are indepenently hydrogen, $C_{1-6}$alkoxy, $C_{1-6}$alkyl, amino, acylamino or substituted acylamino, nitro, halogen, cyano, aldehyde, carboxy, carbamoyl; $R_1$ is a hydrogen or $C_{1-6}$alkyl or R and $R_1$ form together a fused 6-membered heterocyclic ring. The compound is effective in the treatment of congestive heart failure.

6 Claims, No Drawings

HETEROCYCLIC LACTAM COMPOUNDS

This application is a continuation-in-part of copending application Ser. No. 222,754 filed July 22, 1988, which is a continuation of application Ser. No. 139,539 filed Dec. 30, 1987.

BACKGROUND OF THE INVENTION

Field of the Invention

This invention relates to novel heterocyclic lactam compounds and salts thereof useful as cardiotonic agents, antihypertensive agents and vasodilatators for the treatment of congestive heart failure. This invention also relates to processes for preparing the same as well as pharmaceutical compositions comprising these compounds or salts thereof.

SUMMARY OF THE INVENTION

The novel compounds useful as isotopic agents are heterocyclic lactam compounds of formula I or II:

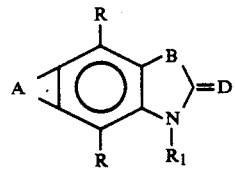

or

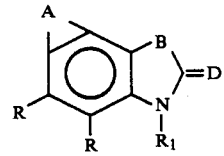

and pharmaceutically acceptable salts thereof, in which A is —N=N—NH—, —X—C($R_2$)=N—, —N=C($R_2$)—X—, —X—CH($R_2$)—C($R_2$)=N— or —N=C($R_2$)—CH($R_2$)—X—, wherein X is sulphur, oxygen or nitrogen and $R_2$ is provided that where two $R_2$-groups are present in the A group one of the $R_2$ groups is hydrogen and the other $R_2$ group and provided that only one $R_2$ group is present, the $R_2$ group is hydrogen, amino, substituted amino, $C_{1-6}$alkyl, substituted acylamino or one of the following groups:

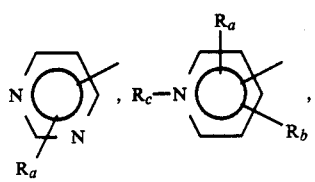

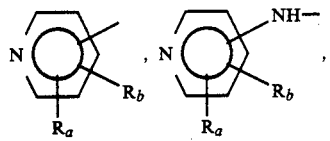

-continued

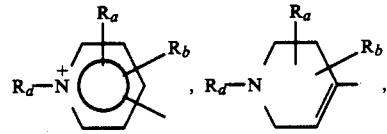

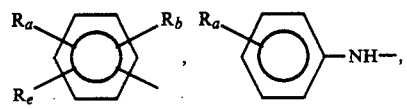

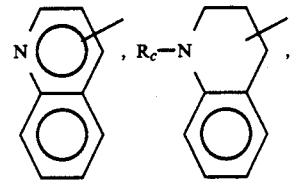

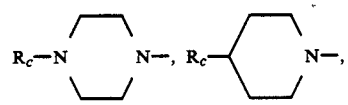

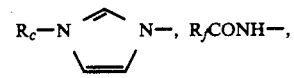

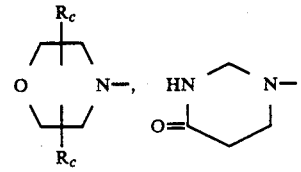

wherein $R_a$ is hydrogen, amino, substituted amino, $C_{1-6}$alkoxy, heterocyclic five membered ring or —NHCOR', wherein R' is $C_{1-6}$alkyl, aryl or heterocyclic five membered ring, $R_b$ is hydrogen, $C_{1-6}$alkoxy, $C_{1-6}$alkylthio or hydroxy, $R_c$ is hydrogen or $C_{1-6}$alkyl or oxygen and $R_d$ is $C_{1-6}$alkyl or oxygen, $R_e$ is hydrogen, hydroxy or $C_{1-6}$alkoxy, $R_f$ is $C_{1-6}$alkyl; B is —($CH_2$)$_m$—C($R_3R_4$)—($CH_2$)$_n$—, —C($R_3$)=CH—, —CH=C($R_3$)—, —O—[C($R_3R_4$)]$_n$—, —[C($R_3R_4$)]$_n$—O—, —S—[C($R_3R_4$)]$_n$— or —[C($R_3R_4$)]$_n$—S— wherein $R_3$ and $R_4$, which can be independently the same or different, are hydrogen, $C_{1-6}$alkyl, aryl (preferably phenyl) or pyridyl and m and n are independently zero or 1; D is either oxygen or sulphur; the two R-groups are independently hydrogen, $C_{1-6}$alkoxy, $C_{1-6}$alkyl, amino acylamino or substituted acylamino, nitro, halogen, cyano, aldehyde, carboxy, carbamoyl; $R_1$ is a hydrogen or $C_{1-6}$alkyl or R and $R_1$ form together a fused 6-membered heterocyclic ring.

In the foregoing definitions, the $C_{1-6}$-alkyl moieties represent methyl, ethyl, straight-chain propyl, butyl, pentyl or hexyl. The alkoxy and alkylthio groups are the corresponding $C_{1-6}$-alkyls attached trough an oxygen-or thio- group. The aryl groups can be phenyl or naphthyl, which can be substituted by one to three methyl groups. The acyl amino groups is a $C_{1-6}$-alkyl-CO-group. Preferred embodiments of the heterocyclic five membered ring include furyl, thienyl, imidazolyl, pyrazolyl, oxazolyl and thiazolyl groups.

DETAILED DESCRIPTION OF THE INVENTION

Congestive heart failure is characterized by a decrease in cardiac output and an increase in right and left ventricular filling pressure. This hemodynamic condition can produce symptoms of dyspnea, fatigue and edema. Treatment of heart disease usually focuses on the three principle factors determining cardiac performance: preload, impedance and an increase in systolic performance (contractility). Vasodilation can improve cardiac function by reducing preload and impedance. Cardiac output can be enhanced by augmenting contractility. This is the rationale for developing inotropic compounds.

In the present invention the preferred structures of new compounds which have particular usefulness as inotropic agents are presented by the following formulas:

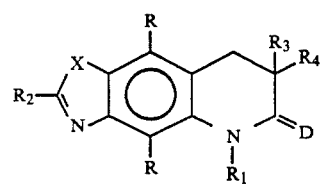
III

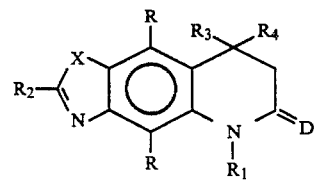
IV

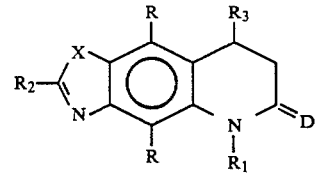
V

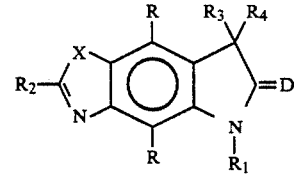
VI

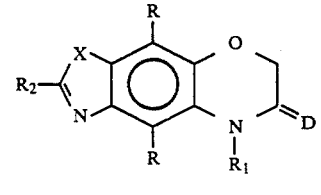
VII

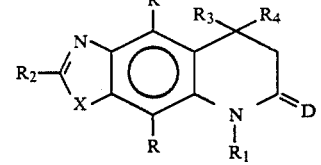
VIII

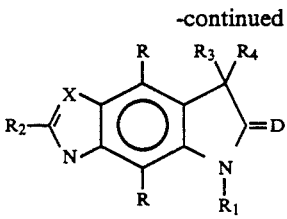
IX

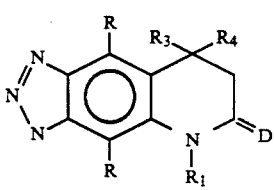
X

The most preferred new compounds of the present invention are presented by the following structures:

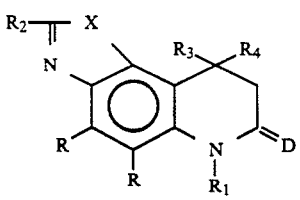
XI

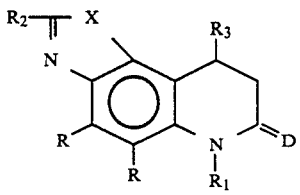
XII

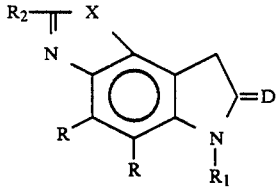
XIII

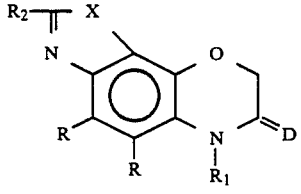
XIV

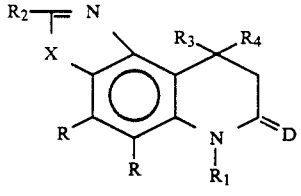
XV

-continued

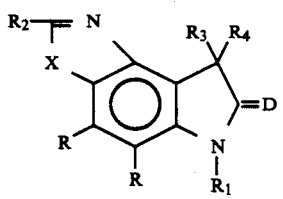

XVI

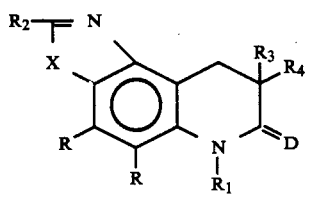

XVII

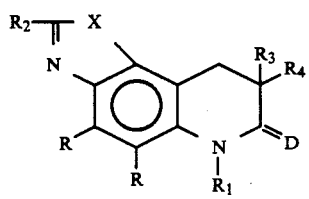

XVIII

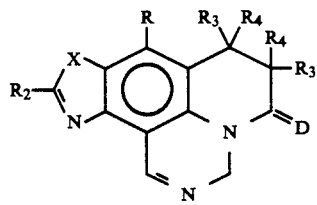

XIX

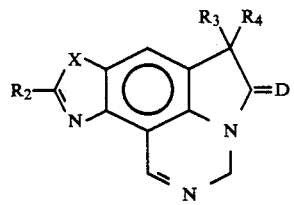

XX

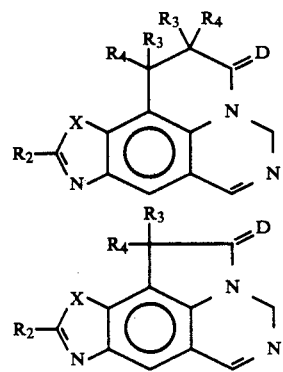

XXI

XXII wherein R, R$_1$, R$_2$, R$_3$, R$_4$, X and D are as defined above.

The compounds of Formula I and II may be prepared in accordance with the following reaction sequences The bicyclic portion of the molecule containing the lactam ring (XXIII),

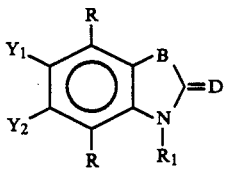

XXIII wherein B, R and R$_1$ are as defined above and Y$_1$ is hydrogen, —OH, —SH or —NH$_2$ when Y$_2$ is —NH$_2$, or Y$_2$ is hydrogen, —OH, —SH or —NH$_2$ when Y$_1$ is —NH$_2$, can be prepared according to methods known in the literature.

Compound XXIII, in the case wherein Y$_1$ is hydrogen and Y$_2$ is amino or contrary Y$_1$ is amino and Y$_2$ is hydrogen, is reacted in the presence of sulphur with a compound having the formula XXIV,

R$_2$—CH$_3$   XXIV wherein R$_2$ is as defined above,
to give the compounds I or II according to the invention, wherein A is —N=C(R$_2$)—S— or —S—C(R$_2$)=N— and R$_2$ is as defined above.

Alternatively the compounds XXIII wherein Y$_1$ is amino and Y$_2$ is hydrogen may be reacted first with the compound having the formula XXV,

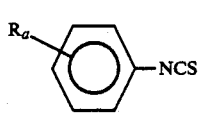

XXV wherein R$_a$ is as defined above, to give the intermediate compound having the formula XXVI

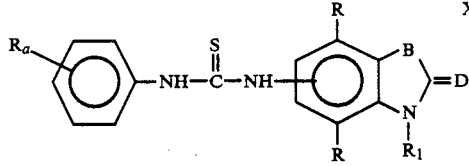

XXVI which compound is then cyclized to the compounds I and II according to the invention with the aid of bromine or sulphur monochloride.

Alternatively the compound XXIII wherein Y$_1$ is —OH, —SH or —NH$_2$ and Y$_2$ is amino or contrary Y$_1$ is amino and Y$_2$ is —OH, —SH or —NH$_2$ may be reacted with the compound having the formula XXVII,

R$_2$—C—Z

XXVII wherein R$_2$ is as mentioned above and Z is —OH, —OR″, wherein R″ is lower alkyl, or halogen to give directly the compounds I or II according to the invention.

The compounds I or II wherein A is —N=C(R$_2$)—CH(R$_2$)—S— or —S—CH(R$_2$)—C(R$_2$)=N— or —N—CH(R$_2$)—C(R$_2$)=N— or —N=C(R$_2$)—C(R$_2$)=N— can be prepared by reacting compound XXIII wherein Y$_1$ is —OH, —SH or —NH$_2$ and Y$_2$ is —NH$_2$ or contrary Y$_1$ is —NH$_2$ and Y$_2$ is —OH, —SH or NH$_2$ with compound having the formula XXVIII,

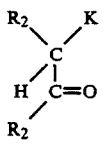

XXVIII wherein K is halogen and $R_2$ is as defined above.

The compounds I or II wherein A is $-N=N-NH-$ may be prepared from XXIII wherein $Y_1$ and $Y_2$ are $-NH_2$ by treating with nitrous acid.

Determination of inotropic activity

The inotropic activity has been determined by the aid of the method described below.

Male or female guinea-pigs (300–400 g) of the Dunkin-Hartley strain were killed by a sharp blow to the head. Their hearts were immediately excised and placed in an oxygenated (95% $O_2$–5%$CO_2$) Krebs-Ringer solution having the following composition (mM): NaCl, 135; KCl, 5; $MgCl_2$ 1; $CaCl_2$, 2; $Na_2HPO_4$, 1; $NaHCO_3$, 15; glucose 10 (pH 7.2–7.4). Right ventricular papillary muscles were dissected out and placed in a 5 ml - temperature-regulated (30°±1° C.) organ bath and continuously suffused with the Krebs-Ringer solution at a rate of 6±1 ml $min^{-1}$. One end of each papillary muscle was fixed to the chamber with syringe needles (26 gauge), while the other was connected via a hooked metal rod to an isometric force transducer (FT.03, Grass Instruments, Quincy, Mass., U.S.A.). The muscles were stretched to a resting tension of 300 mg and were stimulated with bipolar silver electrodes a rate of 0.5 Hz using single square pulses (5–10V, 0.5–1.0 msec) from an analog stimulator (Model S88, Grass) coupled to a constant current (1–10 mA) unit (model PSIU6, Grass). After an equilibration period of 30–45 min, the muscles were consecutively exposed, for 10 min each, to 0.4% DMSO alone and test compounds concentrations of 1, 3, 10 and 30 μM with 0.4% DMSO as the vehicle.

Isometric tension was measured via a low-level D.C. amplifier and a D.C. driver amplifier (Models 7P1F and 7DAG, respectively, Grass). The output was fed into a programmable digitizer (Model 390AD, Tektronix, Beaverton, Oreg., U.S.A.) and connected, via a IEEE-488 bus line and interface to a Professional 380 (PDP-11/70) microcomputer (Digital Equipment Corp., Maynard, Mass., U.S.A.). Data acquisition and analysis was done in real-time using a PASCAL program.

The inotropic response for the test compounds at a concentration of 10 μM is shown in Table 1.

| GUINEA PIG PAPILLARY MUSCLE Force of contraction | |
|---|---|
| Compound | % increase in force of contraction at $10^{-5}$ M as compared to vehicle control (X ± SE) |
| 2-(4-pyridinyl)thiazolo[5,4-g]-7,8-dihydro-6(5H)quinolone | 94.4 ± 10.9 |
| 2-(2-amino-4-pyrimidinyl)thiazolo[5,4-g]-7,8-dihydro-6(5H)quinolone trifluoroacetate | 53.7 ± 18.1 |
| 2-(4-pyridinyl)-5H-thiazolo[4,5-g][1,4]-benzoxazin-6(7H)-one hydrobromide | 59.7 ± 23.8 |
| 2-(2-pyridinyl)thiazolo[5,4-g]-7,8-dihydro-6(5H)quinolone | 80.4 ± 51.1 |
| 2-(1-methyl-1,2,5,6-tetrahydro-4-pyridinyl)-thiazolo[5,4-g]-7,8-dihydro-6(5H)quinolone | 27.4 ± 14.5 |
| 2-(3-pyridinylamino)thiazolo[5,4-g]-7,8-dihydro-6(5H)quinolone | 17.3 ± 9.4 |
| 2-(4-acetamidophenylamino)thiazolo[5,4-g]-7,8-dihydro-6(5H)quinolone | 31.1 ± 18.9 |
| 2-(4-pyridinyl)-6H-thiazolo[5,4-g][1,4]-benzoxazin-7(8H)one hydrobromide | 12.2 ± 6.8 |
| 2-(1-methyl-4-pyridino)thiazolo[5,4-g]-7,8-dihydro-6(5H)quinolone iodide | 4.6 ± 6.4 OBS SD not |
| 2-(4-pyridinyl)-5,5-dimethyl-5H-thiazolo-4,5-g]-7(8H)quinolone hydrobromide + 2-(4-pyridinyl)-9,9-dimethyl-6H-thiazolo-[5,4-f]-7(8H)quinolone hydrobromide | 73.9 ± 25.7 |
| 2-(4-pyridinyl)thiazolo[5,4-g]-4-chloro-7,8-dihydro-6(5H)quinolone | 55.6 ± 18.6 |
| 2-(4-pyridinyl)thiazolo[5,4-g]-4-bromo-7,8-dihydro-6(5H)quinolone | 122.0 ± 48.4 |
| 2-(3-pyridinyl)thiazolo[5,4-g]-7,8-dihydro-6(5H)quinolone | 40.5 ± 30.6 |
| 2-(4-pyridinyl)thiazolo[5,4-g]-4-nitro-7,8-dihydro-6(5H)quinolone | 32.3 ± 16.8 |
| 2-(4-pyridinyl)thiazolo[4,5-f]-6(7H)-quinolone | 73.5 ± 7.5 |
| 2-(4-methyl-1-piperidyl)thiazolo[5,4-g]-7,8-dihydro-6(5H)quinolone | 16.0 ± 11,5 |
| 2-(1-oxido-4-pyridinyl)thiazolo[5,4-g]-4,8,8-trimethyl-7,8-dihydro-6(5H)quinolone | 44.8 ± 13.4 |
| 2-(4-pyridinyl)-7,7-dimethyl-5H-thiazolo-[5,4-f]-6(7H)indolone | 57.2 ± 16.1 |
| 2-(4-pyridinyl)-5H-thiazolo[4,5-f]-6(7H)-indolone | 26.3 ± 7.7 |
| 2-(4-pyridinyl)thiazolo[5,4-g]-5-methyl-7,8-dihydro-6-quinolone | 22.7 ± 27.6 |
| 2-(4-pyridinyl)thiazolo[5,4-g]-7-methyl-7,8-dihydro-6(5H)quinolone hydrobromide methanolate | 62.3 ± 24.4 |
| 2-(4-pyridinyl)thiazolo[5,4-g]-8-methyl-6(5H)quinolone trifluoroacetate | 45.1 ± 15.3 |
| 2-(4-pyridinyl)-8-methyl-7,8-dihydrothiazolo-[5,4-g]-6(5H)quinolone trifluoroacetate | 43.8 ± 9.6 |
| 2-(4-pyridinyl)-4,8,8-trimethyl-7,8-dihydro-thiazolo[5,4-g]-6(5H)quinolone | 48.3 ± 13.8 |
| 2-aminothiazolo[5,4-f]-5H-7-methyl-6(7H)-indolone | 24.3 ± 5.7 |
| 2-(4-pyridinyl)-5,5-dimethyl-5H-thiazolo-[4,5-f]-6(7H)indolone | 18.0 ± 11.8 |
| 2-(4-pyridinyl)thiazolo[5,4-g]-7,8-dihydro-6(5H)quinolinethione | 36.5 ± 14.4 |
| 2-(4-morpholinyl)thiazolo[5,4-g]-7,8-dihydro-6(5H)quinolone | 58.0 ± 45.0 |
| 2-(3,4,5-trimethoxyphenyl)thiazolo[5,4-g]-7,8-dihydro-6(5H)quinolone | 46.0 ± 31.0 |
| triazolo[5,4-g]-7,8-dihydro-6(5H)quinolone | 47.5 ± 15.4 |
| 2-(4-Pyridyl)thiazolo[5,4-g]-8,8-dimethyl-6(5H)quinolone hydrobromide | 16.8 ± 15.6 |
| 2-(4-Pyridinyl)-7-methyl-5H-thiazolo-[5,4-f]-6(7H)indolone | −11.4 ± 7.6 |
| 2-(4-Pyridyl)thiazolo[5,4-g]-4-amino-7,8-dihydro-6(5H)quinolone | 35.0 |
| 2-(N,N-Diethylamino)thiazolo[5,4-g]-7,8-dihydro-6(5H)quinolone | 24.0 |
| 2-(4-Pyridyl)thiazolo[4,5-f]-5,5-dimethyl-8-bromo-6(7H)indolone | 51 ± 36 |
| 2-(4-Pyridyl)thiazolo[5,4-f]-7,7-dimethyl-4-bromo-6(5H)indolone | 75 ± 44 |
| 2-(4-Pyridyl)thiazolo[4,5-f]-5,5-dimethyl-8-formyl-6(7H)indolone | 56 |
| 2-(1-Piperazinyl)thiazolo[5,4-g]-7,8-dihydro-6(5H)quinolone | 32 |
| 2-(4-Pyridyl)thiazolo[5,4-f]-4-chloro-8,9-dihydro-7(6H)quinolone | 56 ± 22 OBS! 3 μM |
| 2-(4-Pyridyl)thiazolo[5,4-f]-7,7-dimethyl-6(5H)indolone | 34 ± 10 |
| 2-(4-Pyridyl)thiazolo[4,5-f]-5,5-dimethyl-8-carboxy-6(7H)indolone | 20 ± 14 |

-continued

GUINEA PIG PAPILLARY MUSCLE
Force of contraction

| Compound | % increase in force of contraction at $10^{-5}$ M as compared to vehicle control (X ± SE) |
| --- | --- |
| 2-(4-Oxo-1-piperidyl)thiazolo[5,4-g]-7,8-dihydro-6(5H)quinolone | 45 ± 11 |
| 2-(4-Pyridyl)thiazolo[5,4-f]-4-chloro-5-nitro-8,9-dihydro-7(6)quinolone | 39 ± 27 |
| 6H-9H-2-(4-Pyridyl)thiazolo[4,5-e]-pyrrolo[3,2,1-h,i]-quinazolin-8-one | 89 ± 27 |
| 6H-2-(4-Pyridyl)thiazolo[4,5-f]-9,10-dihydro-9-methyl-pyrido-[3,2,1-i,j]quinazolin-8-one | 13 |
| 6H-2-(4-Pyridyl)thiazolo[4,5-f]-9,10-dihydro-10-methylpyrido-[3,2,1-i,j]-quinazolin-8-one | 77 ± 7 |
| 6-H-2-(4-Pyridyl)thiazolo[4,5-f]-9,10-dihydropyrido-[3,2,1-i,j]quinazolin-8-one | 69 ± 34 |
| 7H-2-(4-Pyridyl)thiazolo[4,5-g]-4-cloro-9,10-dihydropyrido-[3,2,1-i,j]-quinazolin-8-one | 51 ± 25 |

The following examples illustrate the invention in greater detail

EXAMPLE 1

2-(4-Pyridinyl)thiazolo[5,4-g]-7,8-dihydro-6(5H)quinolone

A mixture containing 3,6 g of 7-amino-3,4-dihydro-2(1H)quinolone and 2,5 g of sulfur in 7,5 ml of 4-picoline was heated for 5-6 h at 160° C. After cooling the mixture was filtered, washed first with small amount of 4-picoline and then with ether. The crude product was recrystallized from DMF. Yield 5,0 g (80%), m.p. 309°-314° C.

EXAMPLE 2

2-(2-Pyridinyl)thiazolo[5,4-g]-7,8-dihydro-6(5H)quinolone

The procedure described in Example 1 was repeated by using 2-picoline. Yield 2,1 g (33%), m.p. 246°-247° C.

EXAMPLE 3

2-(2-Amino-4-pyrimidinyl)thiazolo[5,4-g]-7,8-dihydro-6(5H)quinolone trifluoroacetate The procedure described in Example 1 was repeated by using 1,2 g of 7-amino-3,4-dihydro-2(1H)quinolone, 0,83 g of sulfur and 1,61 g of 2-amino-4-methylpyrimidine in 2,5 ml of DMA. After cooling the mixture was diluted with methanol and filtered. The crude product was dissolved in boiling trifluoroacetic acid, filtered and diluted with 2-propanol. Yield 0,3 g (10%), m.p. 350° C. (decomp.).

EXAMPLE 4

2-(2-Amino-4-pyridinyl)thiazolo[5,4-g]-7,8-dihydro-6(5H)quinolone

The procedure described in Example 1 was repeated by using 2-amino-4-picoline. Yield 0,64 g (29%), m.p. 350° C. (decomp.)

EXAMPLE 5

2-(4-Acetamidophenylamino)thiazolo[5,4-g]-7,8-dihydro-6(5H)quinoline (a) 7-Isothiocyanato-3,4-dihydro-2(1H)quinolone To a suspension containing 5,4 g of 7-amino-3,4-dihydro-2(1H)quinolone in 70 ml of water was added while stirring and cooling (0° C.) 4.0 ml of thiophosgene. Stirring was continued for 45 min at room temperature and product filtered and washed with water. Yield 5.8 g (87%).

(b) 7-[3(4-Acetamidophenyl)thioureido]-3,4-dihydro-2(1H)quinolone

A solution containing 0.8 g of 7-isothiocyanato-3,4-dihydro-2(1H)quinolone and 0.59 g of 4-acetamidoaniline in 10 ml of THF was stirred for 5 h at room temperature. The product was filtered, dried and used as such to the next step. Yield 0.45 g (32%).

(c) 2-(4-Acetamidophenylamino)thiazolo[5,4-g]-7,8-dihydro-6(5H)quinolone

The above product 0.45 g was dissolved in 5 ml of DMF and 0.065 ml of bromine was added. The solution was stirred for 1 h. THF was added, the product filtered and dissolved in DMSO. The free base was liberated with conc. ammonia, filtered and washed with water, m.p. 190°-195° C.

EXAMPLE 6

2-(1-Methyl-4-pyridino)thiazolo[5,4-g]-7,8-dihydro-6(5H)quinolone iodide

To a solution containing 0.5 g of the compound obtained in Example 1 in 150 ml of DMF 2 ml of methyliodide was added. The solution was heated for 24 h at 50° C. The solvent was evaporated in vacuo and the residue triturated with acetone and filtered. The crude product was dissolved in 140 ml of boiling methanol and filtered. After cooling the crystals were filtered and dried. Yield 0.35 g, m.p. 340° C. (decomp.).

EXAMPLE 7

2-(1-Methyl-1,2,5,6-tetrahydro-4-pyridinyl)-thiazolo[5,4-g]-7,8-dihydro-6(5H)quinolone.

The above product (0.33 g) was suspended in 20 ml of methanol and 1.0 g of sodium borohydride was gradually added while stirring. The solution was stirred further for 30 min after which water was added. The product was filtered, washed with water and recrystallized from acetone. Yield 0.04 g, m.p. 228°-238° C.

EXAMPLE 8

7-Amino-6-mercapto-3,4-dihydro-2(1H)quinolone hydrochloride

To a solution containing 11,0 g of 3-chloro-4,6dinitrophenypropionic acid in 100 ml of ethanol, 5.6g of sodiumsulfide nonahydrate and 0,8 g of sulphur in 5 ml of water were added. The solution was stirred for 1 h at 60° C. and cooled The intermediate product, bis(3-carboxyethyl-4,6-dinitrophenyl) disulfide, was filtered, washed with water and dissolved in 150 ml of 90% acetic acid. 15,0 g of zinc dust was gradually added while stirring at room temperature. The mixture was then refluxed for 30 min and filtered. The filtrate was saturated with gaseous hydrogen chloride, concentrated in vacuo and ether was added. The product was filtered. Yield 4,8 g, m.p. 177° C.

EXAMPLE 9

2-(4-Acetamidophenyl)thiazolo[5,4-g]-7,8-dihydro-6(5H)quinolone

A mixture containing 2,31 g of 7-amino-6-mercapto-3,4-dihydro-quinolone and 1,8 g of 4-acetamidobenzoic acid in 15 ml of polyphosphonic acid, was heated for 2 h at 100°-120° C. After cooling water was added and the product was filtered and washed with water. Yield 2,73 g (81%).

EXAMPLE 10

2-(3,4-Dimethoxyphenyl)thiazolo[5,4-g]-7,8-dihydro-6(5H)quinolone

The procedure described in Example 9 was repeated by using 3,4-dimethoxybenzoic acid instead of 4-acetamidobenzoic acid. Yield 76%.

EXAMPLE 11

2-(3-Pyridinyl)thiazolo[5,4-g]-7,8-dihydro-6(5H)quinolone

The procedure described in Example 9 was repeated by using nicotinic acid instead of 4-acetamidobenzoic acid. Yield 65%.

EXAMPLE 12

2-[4-(1-Imidazolyl)phenyl]thiazolo[5,4-g]-7,8-dihydro-6(5H)quinolone

The procedure described in Example 9 was repeated by using 4-(1-imidazolyl)benzoic acid instead of 4-acetamidobenzoic acid. Yield 57%.

EXAMPLE 13

2-(3-Pyridinylamino)thiazolo[5,4-g]-7,8-dihydro-6(5H)quinolone

A solution containing 3,04 g of 7-isothiocyanato-3,4-dihydro-2(1H)quinolone and 0,94 g of 3-aminopyridine in 30 ml of THF was stirred for 5 h at room temperature The product was filtered and dissolved in 50 ml of DMF 0,6 ml of bromine was added and the solution was stirred for 1 h. THF was added, the product filtered and dissolved in DMSO. The free base was liberated with conc. ammonia, filtered and washed with water M.p.350° C. (decomp.).

EXAMPLE 14

2-(4-Pyridinyl)thiazolo[5,4-g]-7-methyl-7,8-dihydro-6(5H)quinolone

The procedure described in Example 1 was repeated by using 4 ml of 4-picoline, 1,8 g of sulphur and 1,8 g of 7-amino-3-methyl-3,4-dihydro-2(1H)quinolone. Yield 1,2 g, m.p. 287°-292° C.

EXAMPLE 15

2-(4-Pyridinyl)-5H-thiazolo[4,5-g][1,4]-benzoxazin-6(7H)-one hydrobromide

The procedure described in Example 1 was repeated by using 3 ml of 4-picoline, 0,5 g of sulphur and 0,82 g of 6-amino-4H-1,4-benzoxazin-2-one to give 0,87 g of the intermediate compound, 6-(4-pyridinylthiocarbonylamino)-4H-1,4-benzoxazin-2-one, which is dissolved in 20 ml of DMF. 0,16 ml of bromine was added and the solution was heated for 20 min at 100°-120° C. After cooling the product was filtered, washed with DMF and acetone to give 0,6 g of the title compound, m.p. 355° C.

EXAMPLE 16

2-(4-Pyridinyl)-5H-thiazolo[4,5-g][1,4]-benzothiazin-6(7H)-one hydrobromide

The same procedure described in Example 15 was repeated by using 6-amino-4H-1,4-benzothiazin-2-one instead of 6-amino-4H-1,4-benzoxazin-2-one. Mp. 299°-306° C.

EXAMPLE 17

2-(4-Pyridinyl)-6H-thiazolo[5,4-g][1,4]-benzoxazin-7(8H)one hydrobromide

The same procedure described in Example 15 was repeated by using 7-amino-4H-1,4-benzoxazin-2-one instead of 6-amino-4H-1,4-benzoxazin-2-one. Mp 350° C.

EXAMPLE 18

2-(4-Pyridinyl)-4-methoxy-8-methyl-6H-thiazolo[4,5-h][1,4]-benzoxazin-7(8H)one hydrobromide The same procedure described in Example 15 was repeated by using 7-amino-6-methoxy-2-methyl-4H-1,4-benzoxazin-2-one instead of 6-amino-4H-1,4-benzoxazin-2-one. Mp. 304°-305° C.

EXAMPLE 19

2-(4-Pyridinyl)-5H-thiazolo[4,5-f]-6(7H)indolone

The procedure described in Example 1 was repeated by using 5-amino-2(1H)indolone instead of 7-amino-3,4-dihydro-2(1H)quinolone. Mp. 350° C.

EXAMPLE 20

2-(4-Pyridinyl)-7-methyl-5H-thiazolo[5,4-f]-6(7H)indolone

The procedure described in Example 1 was repeated by using 6-amino-3-methyl-2(1H)indolone instead of 7-amino-3,4-dihydro-2(1H)quinolone. Mp. >350° C.

EXAMPLE 21

2-(4-Pyridinyl)-7,7-dimethyl-5H-thiazolo[4,5-f]-6(7H)indolone

The procedure described in Example 1 was repeated by using 5-amino-3,3-dimethyl-2(1H)indolone. Mp. 316° C.

EXAMPLE 22

A mixture of
2-(4-Pyridinyl)-5,5-dimethyl-5H-thiazolo-[4,5-g]-7(8H)quinolone hydrobromide and
2-(4-pyridinyl)-9,9-dimethyl-6H-thiazolo[5,4-f]-7(8H)quinolone hydrobromide.

The procedure described in Example 15 was repeated by using 6-amino-4,4-dimethyl-3,4-dihydro-2(1H)quinolone as a starting material. Mp. 216°-222° C.

EXAMPLE 23

2-(4-Pyridinyl)-8-methyl-7,8-dihydrothiazolo[5,4-g]-6(5H)quinolone trifluoroacetate The procedure described in Example 1 was repeated by using 7-amino-4-methyl-2(1H)-quinolone and 4-picoline as starting materials. Mp. 275°-280° C.

EXAMPLE 24

2-(4-Pyridinyl)-4,8,8-trimethyl-7,8-dihydrothiazolo[5,4-g]-6(5H)quinolone

The method described in Example 1 was repeated by using 7-amino-4,4,8-trimethyl-2(1H)quinolone as starting material. Mp. 305°-307° C.

EXAMPLE 25

2-(4-Pyridinyl)thiazolo[5,4-h]-6,7,8,9-tetrahydro-5-benzazepin-6(5H)-one

The procedure described in Example 1 was repeated by using 8-amino-2,3,4,5-tetrahydro-1-benzazepin-2(1H)-one as starting material. Yield 85%.

EXAMPLE 26

2-(4-Acetamidophenylamino)thiazolo[5,4-g]-7,8-dihydro-6(5H)quinolone (a) 7-[3(4-Acetamidophenyl)thioureido]-3,4-dihydro-2(1H)quinolone A mixture containing 1.92 g of 4-acetamidophenylisothiocyanate and 1.62 g of 7-amino-3,4-dihydro-2(1H)quinolone in 10 ml of DMF was stirred for 6 h at 20° C. Water was added and the product filtered and washed with water. Yield 85%.

(b) 2-(4-Acetamidophenylamino)thiazolo[5,4-g]-7,8-dihydro-6(5H)quinolone

The above product 0.45 g was dissolved in 5 ml of DMF and 0.065 ml of bromine was added. The solution was stirred for 1 h. THF was added, the product filtered and dissolved in DMSO. The free base was liberated with conc. ammonia, filtered and washed with water, m.p. 190°-195° C.

EXAMPLE 27

2-(4-Morpholino)thiazolo[5,4-g]-7,8-dihydro-6(5H)quinolone

A solution containing 0,2 g of 2-chlorothiazolo[5,4-g]-7,8-dihydro-6(5H)quinolone in 5 ml of morpholine was refluxed for 5 h. The express of morpholine was evaporated in vacuo and the residue was treated water. The crystals were filtered and washed with ether, yield 0,1 g, m.p. 275° C.

EXAMPLE 28

2-(4-Methyl-1-piperazinyl)thiazolo[5,4-g]-7,8-dihydro-6(5H)quinolone

The same procedure described in Example 27 was repeated using 1-methylpiperazine instead of morpholine. Yield 0.12 g, m.p. 200°-205° C.

EXAMPLE 29

2-(N,N-Diethylamino)thiazolo[5,4-g]-7,8-dihydro-6(5H)quinolone

The above process was repeated by using diethylamine. Yield 0.11 g, m.p. 205°-210° C.

EXAMPLE 30

2-(1-Imidazolyl)thiazolo[5,4-g]-7,8-dihydro-6(5H)-quinolone

The above process was repeated by using imidazole. Yield
0,08 g, m.p. 268°-272° C.

EXAMPLE 31

2-(1-Piperazinyl)thiazolo[5,4-g]-7,8-dihydro-6(5H)quinolone

The above process was repeated by using piperazine, m.p. 273°-275° C.

EXAMPLE 32

2-(2,6-Dimethyl(-4-morpholino)thiazolo[5,4-g]-7,8-dihydro-6-(5H)quinolone

The above process was repeated by using 2,6-dimethylmorpholine, m.p. 230° C.

EXAMPLE 33

2-(3-Oxo-1-piperazinyl)thiazolo[5,4-g]-7,8-dihydro-6(5H)quinolone

The above process was repeated by using 2-piperazinone, m.p. >300° C.

EXAMPLE 34

2-(4-Pyridylmethylamino)thiazolo[5,4-g]-7,8-dihydro-6(5H)quinolone

The above process was repeated by using 4-aminomethylpyridine, m.p. 229°-232° C.

EXAMPLE 35

2-(4-Oxo-1-piperidyl)thiazolo[5,4-g]-7,8-dihydro-6(5H)quinolone

The above process was repeated by using 4-piperidone ethylene ketal. The intermediate ketal derivative was hydrolysed with 2 molar hydrochloric acid for 1 h at 100° C. The reaction mixture was evaporated to dryness in vacuo and treated with ethyl acetate, m.p. 270°-275° C.

EXAMPLE 36

2-Acetamidothiazolo[5,4-g]-7,8-dihydro-6(5H)quinolone

A solution containing 2.28 g of the product obtained in example 61 in 10 ml of acetic anhydride was heated for 1 h at 120° C. The solvent was evaporated in vacuo and residue treated with ether. Yield 0.5 g, m.p. >250° C. (decomp.).

EXAMPLE 37

2-(4-Methoxyphenyl)thiazolo[5,4-g]-7,8-dihydro-6(5H)quinolone

The process described in Example 10 was repeated by using 4-methoxybenzoic acid, m.p. 330°-335° C.

EXAMPLE 38

2-(4-Methylthiophenyl)thiazolo[5,4-g]-7,8-dihydro-6(5H)quinolone

The process described in Example 10 was repeated by using 4-methylthiobenzoic acid, m.p. >250° C.

EXAMPLE 39

2-Phenylthiazolo[5,4-g]-7,8-dihydro-6(5H)quinolone

The process described in Example 10 was repeated by using benzoic acid, m.p. >250° C.

EXAMPLE 40

2-methylthiazolo[5,4-g]-7,8-dihydro-6(5H)quinolone

The process described in Example 47 was repeated by using acetaldehyde instead of 3,4,5-trimethoxybenzaldehyde, m.p. >250° C.

EXAMPLE 41

2-(4-Pyridyl)thiazolo[5,4-g]-8-methyl-6(5H)quinolone trifluoroacetate

A mixture containing 1,17 g of 7-amino-4-methyl-2(1H)quinolone, 0.75 g of sulphur and 3.0 ml of 4-picoline was heated for 7 h at 160° C. The reaction mixture was treated with methanol and the product was filtered, washed with methanol and dissolved in DMF. 1 ml of sulphur monochloride was added and the mixture was stirred for 15 min at room temperature. The product was filtered and washed with DMF and carbondisulphide and triturated then with trifluoroacetic acid. Sulphur was filtered off and to the filtrate 2-propanol was added. The solution was concentrate in vacuo, the crystals were filtered and washed with 2-propanol, m.p. >350° C.

EXAMPLE 42

2-(4-Hydroxyphenyl)thiazolo[5,4-g]-7,8-dihydro-6(5H)quinolone

The compound described in Example 37 was demethylated by refluxing in hydrobromic acid, m.p. >350° C.

EXAMPLE 43

2-(4-Pyridyl)thiazolo[5,4-g]-4-bromo-7,8-dihydro-6(5H)quinolone

The compound described in Example 1 was treated with bromine in DMF at room temperature. Dil. ammonium hydroxide solution was then added. The product was filtered and washed with water, m.p. 299°-300° C.

EXAMPLE 44

2-(4-Pyridyl)thiazolo[5,4-g]-4-chloro-7,8-dihydro-6(5H)quinolone

To a solution containing 0,42 g of the compound described in Example 1 in 10 ml of DMF, 0,2 g of N-chlorosuccinimide and catalytic amount of 3-chloroperoxybenzoic acid were added. The mixture was heated for 5 min at 150° C. After cooling to 70° C. the product was filtered and washed with DMF and acetone. Yield 0,35 g, m.p. 330°-333° C.

EXAMPLE 45

2-(4-Pyridinyl)thiazolo[5,4-g]-4-nitro-7,8-dihydro-6(5H)quinolone

To a solution containing 0.56 g of the compound described in Example 1 in 5 ml conc. sulphuric acid an equivalent amount of conc. nitric acid was added at room temperature. The solution was stirred for 4 h at 20° C. and poured the to ice-water. The solution was neutralized with NH4OH. The product was filtered and washed with water. Yield 0.58 g, 284°-289° C.

EXAMPLE 46

2-(4-Pyridyl)thiazolo[5,4-g]-4-amino-7,8-dihydro-6(5H)quinolone

The compound obtained in Example 45 was dissolved in conc. hydrochloric acid and treated with stannous chloride solution in conc. hydrochloric acid. The mixture was stirred for 45 min at room temperature. The product was filtered and washed with conc. hydrochloric acid. The free base was liberated in boiling NaOH-solution. The product was filtered and washed with water, m.p. 341°-346° C.

EXAMPLE 47

2-(3,4,5,-Trimethoxyphenyl)thiazolo[5,4-g]-7,8-dihydro-6(5H)quinolone

A mixture containing 0.32 g of 7-amino-3,4-dihydro-2-(1H)quinolone, 0,39 g of 3,4,5-trimethoxybenzaldehyde and 0,13 g of sulphur in 2 ml of DMF was stirred for 6 h at 160° C. The reaction mixture was filtered and washed with DMF and ether, Yield 0,3 g, m.p. 289°-292° C.

EXAMPLE 48

2-(4-Pyridyl)thiazolo[5,4-f]-4-chloro-8,9-dihydro-7(6H)quinolone

A mixture containing 0,5 g of 6-amino-7-chloro-3,4-dihydro-2(1H)quinolone, 0,3 g of pyridine-4-carboxaldehyde and 0.16 g of sulphur in 2 ml of DMA was heated for 2 h at 170° C. After cooling 15 ml of methanol was added and sulphur was filtered off. To the filtrate 0.15 ml of bromine was added. The precipitate was filtered and washed with methanol. Yield 0,35 g, m.p. >350° C.

EXAMPLE 49

2-(4-Pyridyl)thiazolo[4,5-f]-7(6H)quinolone

A mixture containing 0,4 g of 5-amino-2(1H)quinolone 3,0 ml of 4-picoline and 0,32 g of sulphur was heated for 6 h at 160° C. The mixture was filtered and the precipitate was dissolved in DMF after which 0.035 ml of bromine was added. The solution was stirred for 1 h at room temperature, filtered and the product washed with DMF and acetone. Yield 0,15 g, m.p. >350° C.

EXAMPLE 50

Triazolo[5,4-g]-7,8-dihydro-6(5H)quinolone

To solution containing 1,4 g 6-amino-3-methyl-7-(4-pyridinethiocarboxamino)-2(1H)quinolone in 50 ml 1 mol hydrochloric acid 4,0 g of sodium nitrite was gradually added with stirring and cooling at 0°-5° C. The solution was warmed to room temperature and made first basic with NaOH and then acidic with hydrochloric acid. Finally the pH was adjusted to 8.0 with NaHCO3. The solution was extracted with ethyl acetate. The solvent was evaporated in vacuo and the residue was crystallized from acetone-dichloromethane by adding petroleum ether. Yield 0,3 g, mp 155° C. (decomp.)

EXAMPLE 51

2-(4-Pyridyl)thiazolo[5,4-g]-7-methyl-7,8-dihydro-6(5H)quinolone hydrobromide methanolate A mixture of 1.4 g of 7-amino-3-methyl-2(1H)quinolone, 4 ml of 4-picoline and 1-2 g of sulphur was heated for 4 h at 160° C. To the reaction mixture 20 ml of MeOH was added and the precipitate was filtered. The intermediate product was dissolved in DMF and 0,2 ml of bromine was added. The mixture was stirred for 2 h at room temperature, diluted with ether and filtered. Yield 1,2 g, m.p. 287°-292° C.

EXAMPLE 52

2-Aminothiazolo[5,4-f]-7-methyl-6(5H)indolone

To a solution containing 1.62 g of 6-amino-3-methyl-2(1H)indolone and 1,7 g of sodium thiocyanate in 20 ml of anhydrous acetic acid 0.52 ml of bromine in 5.1 of anhydrous acetic acid was gradually added with stirring and cooling (20° C.). The mixture was stirred 15 min more at room temperature and poured then to 100 ml of water. The product was filtered and washed with water. Yield 1,3 g.

EXAMPLE 53

2-(4-Pyridyl)thiazolo[5,4-f]-4-chloro-5,9,9-trimethyl-8,9-dihydro-7(6H)quinolone trifluoroacetate A mixture containing 1,2 g of 6-amino-7-chloro-4,4,8-trimethyl-2(1H)quinolone and 0,48 g sulphur in 5 ml of 4-picoline was refluxed for 2,5 h. The excess of 4-picoline was evaporated in vacuo. The residue was dissolved in 25 ml of DMF and treated with 0,26 ml of bromine under cooling (0° C.). The mixture was heated for 10 min at 100° C., cooled to 0° C. The precipitate was filtered and washed with DMF and acetone. The product was suspended in NaHCO$_3$ solution, filtered and washed with water. The crude free base was dissolved in DMSO and treated with trifluoroacetic acid and the product was filtered and washed with DMSO and acetone, m.p. 335°–340° C.

EXAMPLE 54

2-(4-Pyridyl)thiazolo[5,4-f]-4-cloro-7(6H)quinolone

To a solution containing 0.78 g of the product obtained in Example 48 was dissolved in 5 ml of conc. H$_2$SO$_4$ 0,14 ml of conc. nitric acid was added with stirring for 24 h at 50° C. The reaction mixture was poured in cold water and washed with NaHCO$_3$ solution and water, m.p. >350° C.

EXAMPLE 55

2-(4-Pyridyl)thiazolo[4,5-f]-5,5-dimethyl-6(7H)indolone

To a solution containing 2,95 g of 3,3-dimethyl-5-(4-pyridinethiocarboxamido)-2(1H)indolone in 15 ml of DMF 1,2 ml of sulphur monochloride was gradually added. The mixture was stirred for 15 min at room temperature. The product was filtered and washed with carbon disulfide and dichloromethane. Yield 1.9 g, m.p. 249°–251° C.

EXAMPLE 56

2-(4-Pyridyl)thiazolo[5,4-f]-7,7-dimethyl-4-formyl-6(5H)indolone

A mixture containing 2,12 g of 6-amino-3,3-dimethyl-2(1H)-indolone hydrochloride and 1,28 g of sulphur in 4 ml of 4-picoline was heated for 3 h at 160° C. The mixture was filtered and washed with carbon disulfide and acetone, m.p. 311°–316° C.

EXAMPLE 57

2-(4-Pyridyl)thiazolo[5,4-g]-8,8-dimethyl-6(5H)quinolone hydrobromide

To a solution containing 1,0 g of 4,4-dimethyl-7-(4-pyridinethiocarboxamido)-3,4-dihydro-2(1H)quinolone in 5 ml of pyridine 0,39 ml of sulphur monochloride was added. The mixture was stirred for 30 min at room temperature. The precipitate was filtered and washed with carbon disulfide and acetone. Yield 0,1 g, m.p. 294°–295° C.

EXAMPLE 58

2-(4-Pyridyl)thiazolo[5,4-g]-7,8-dihydro-6-thioxo-(5H)quinolone

A mixture containing 1 g of the product obtained in Example 1 and 1 g of phosphorus pentasulfide in 10 ml of pyridine was refluxed for 1 h. 1 molar hydrochloric acid was added the product was filtered and washed with water. The product was suspended in dil. NH OH, stirred for 30 min and the free base was filtered. Yield 0,3 g, m.p. 335°–340° C.

EXAMPLE 59

2-(4-Pyridyl)thiazolo[5,4-g]-7,8-dihydro-5-methyl-6-quinolone

To a mixture containing 1.8 g of the product obtained in Example 1 in 20 ml of DMF 0,51 g of sodium hybrid dispersion in mineral oil (50%) was added with stirring at room temperature. After 2 h 1 ml of methyl iodide was added and the mixture was stirred further for 20 min at 20° C. 150 ml of dichloromethane was then added. The solution was washed with dil. NH$_4$OH. The solvent was evaporated in vacuo and the residue triturated with acetone and filtered. Yield 0.43 g, m.p. 216°–222° C.

EXAMPLE 60

2-(1-Oxide-4-pyridyl)thiazolo[5,4-g]-7,8-dihydro-4,8,8-trimethyl-6(5H)quinolone

To a suspension containing 0,16 g of the product obtained in Example 24 in 5ml of DMF 0,2 g of 3-chloroperoxybenzoic acid was added. The mixture was stirred over night at room temperature. The product was filtered and washed with DMF and acetone. Yield 0,09 g, m.p. 279°–283° C.

EXAMPLE 61

2-Aminothiazolo[5,4-g]-7,8-dihydro-6(5H)quinolone

To a solution containing 5,0 g of 7-amino-2(1H)quinolone and 5,25 g of sodium thiocyanate in 25 ml of anhydrous acetic acid 1,5 ml of bromine was gradually added with stirring at room temperature. The mixture was stirred 15 min more and filtered. The product was dissolved in 6 mol hydrochloric acid heated for 30 min at 100° C. The pH was then adjusted 7,00 with sodium hydroxide solution. The precipitate was filtered and washed with water and acetone. Yield 1.86 g, m.p. >250° C. (decomp).

EXAMPLE 62

6H-9H-2 (4-Pyridyl)thiazolo[4,5-e]-g,g-dimethyl-pyrrolo[-3,2,1-h,i]quinazolin-8-one A mixture containing 1,0 g of the compound obtained in Example 56 and 1,0 g hexamethylenetetramine in 10 ml of trifluoroacetic acid was refluxed for 2 h. To the boiling solution 7 ml of water was added and the solution was evaporated to dryness. To the residue 10 ml of water was added and the pH was adjusted to 5 with NaOH-solution. The product was filtered and washed with water m.p. 250°–255° C.

EXAMPLE 63

6H-2-(4-Pyridyl)thiazolo[4,5-f]-9,10-dihydropyrido-[3,2,1-i,j]quinazolin-8-one

The same process described in Example 62 was repeated by using 2-(4-pyridyl)thiazolo[5,4-g]-7,8-dihydro-6(5H)quinolone as starting material. Yield 46%, m.p. 273°–275° C.

EXAMPLE 64

6H-2-(4-Pyridyl)thiazolo[4,5-f]-9,10-dihydro-10-methylpyrido-[3,2,1-i,j]quinazolin-8-one The process described in Example 62 was repeated by using 2-(4-pyridyl)thiazolo[5,4-g]-7,8-dihydro-8-methyl-6(5H)-quinolone as starting material. Yield 40%, m.p. 266°–271° C.

EXAMPLE 65

6H-2-(4-Pyridyl)thiazolo[4,5-f]-9,10-dihydro-9-methylpyrido[3,2,1-i,j]quinazolin-8-one The process described in Example 62 was repeated by using 2-(4-pyridyl)thiazolo[5,4-g]-7,8-dihydro-7-methyl-6(5H)-quinolone as starting material. Yield 27%, m.p. 247°–251° C.

EXAMPLE 66

7H-2-(4-Pyridyl)thiazolo[4,5-g]-4-chloro-9,10-dihydropyrido-[3,2,1-i,j]quinazolin-8-one The process described in Example 62 was repeated by using 2-(4-pyridyl)thiazolo[5,4-f]-4-chloro-7,8-dihydro-6(5H)-quinolone as starting material. Yield 33%, m.p. 276°–280° C.

EXAMPLE 67

2-(4-Pyridyl)thiazolo[4,5-f]-5,5-dimethyl-8-formyl-6(7H)indolone

The process described in Example 62 was repeated by using 2-(4-pyridyl)-thiazolo[4,5-f]-5,5-dimethyl-6(7H)indolone as starting material, m.p. >300° C. (decomp).

EXAMPLE 68

8H-8,8-dimethyl-3-phenyl-1,2-dihydro-pyrazino[2,3-f]-7(6H)indolone

A solution containing 0,4 g of 5,6-diamino-3,3-dimethyl-2(1H)indolone, 0,4 g of 2-bromoacetophenone and 0,2 g of sodium acetate in 10 ml of MeOH was stirred under nitrogen for 2 h at room temperature. The product was filtered and washed with water. Yield 0.32 g (53%), m.p.233°–235° C.

EXAMPLE 69

8H-8,8-dimethyl-3-phenylpyrazino[2,3-f]-7(6H)indolone

To a solution of 0,28 g of the product obtained in Example 68 in 15 ml of acetone-water (1:1) 0,34 g of 2,3-dichloro-5,6-dicyano-1,4-benzoquinone was added. The mixture was stirred for 90 min at 100° C. Water was added and the product was filtered and washed with water. Yield 0,2 g, m.p. 249°–253° C.

We claim:

1. A compound of the formula

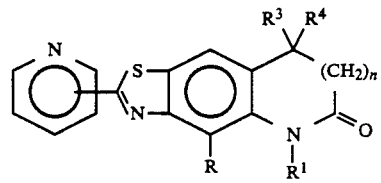

and pharmaceutically acceptable salts thereof, wherein n=0 or 1, R is hydrogen or halogen, $R^1$ is hydrogen, or where R and $R^1$ combine to form a

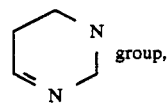 group, and $R^3$ and $R^4$ are hydrogen or $C_{1-6}$-alkyl.

2. A compound according to claim 1, wherein the structure of the compound is

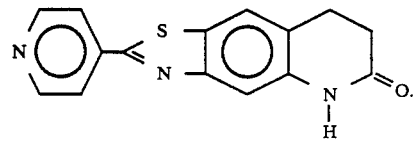

3. A compound according to claim 1, wherein the structure of the compound is

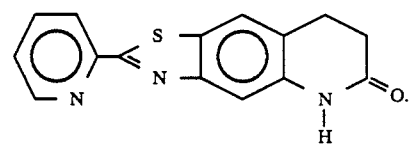

4. A compound according to claim 1, wherein the structure of the compound is

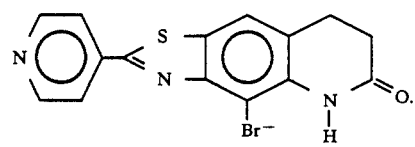

5. A compound according to claim 1, wherein the structure of the compound is

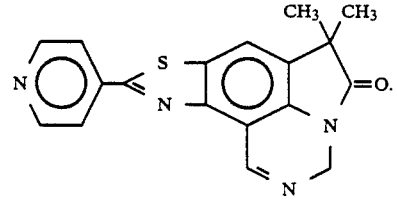

6. A compound according to claim 1, wherein the structure of the compound is

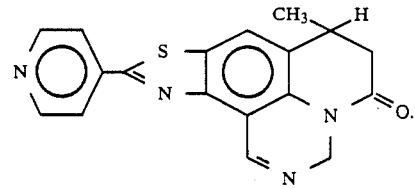

* * * * *